United States Patent
Fatiny (10) Patent No.: US 9,456,885 B2
(45) Date of Patent: Oct. 4, 2016

(54) ERGONOMIC SEMI-AUTOMATIC ROTATABLE TOOTHBRUSH APPARATUS

(71) Applicant: UMM AL-QURA UNIVERSITY, Makkah (SA)

(72) Inventor: Fahad Ibrahim Fatiny, Makkah (SA)

(73) Assignee: Umm Al-Qura University, Makkah (SA)

( * ) Notice: Subject to any disclaimer, the term of this patent is extended or adjusted under 35 U.S.C. 154(b) by 101 days.

(21) Appl. No.: 14/417,914

(22) PCT Filed: Jan. 15, 2015

(86) PCT No.: PCT/IB2015/000031
§ 371 (c)(1),
(2) Date: Jan. 28, 2015

(87) PCT Pub. No.: WO2016/113582
PCT Pub. Date: Jul. 21, 2016

(65) Prior Publication Data
US 2016/0206414 A1     Jul. 21, 2016

(51) Int. Cl.
*A46B 9/04* (2006.01)
*A61C 17/22* (2006.01)
*A46B 5/02* (2006.01)
*A46B 5/00* (2006.01)

(52) U.S. Cl.
CPC ......... *A61C 17/225* (2013.01); *A46B 5/0083* (2013.01); *A46B 5/02* (2013.01); *A61C 17/222* (2013.01)

(58) Field of Classification Search
CPC .. A46B 5/0083; A46B 5/0087; A46B 5/002; A46B 5/02; A46B 5/00; A46B 5/0075; A46B 5/0095; A61C 17/225
See application file for complete search history.

(56) References Cited

U.S. PATENT DOCUMENTS

| | | | |
|---|---|---|---|
| 4,106,152 A | 8/1978 | Hadary | |
| 4,209,871 A | 7/1980 | Ernest et al. | |
| 4,598,437 A | 7/1986 | Ernest et al. | |
| 7,954,196 B1 | 6/2011 | Nault-Richter | |
| 8,359,697 B2* | 1/2013 | Wang | A46B 5/00 15/167.1 |
| 8,561,248 B2 | 10/2013 | Fatiny | |
| 8,813,300 B2 | 8/2014 | Woo et al. | |
| 2009/0113650 A1* | 5/2009 | Flek, Jr. | A46B 5/02 15/167.1 |
| 2012/0090108 A1 | 4/2012 | Woo et al. | |

FOREIGN PATENT DOCUMENTS

| | | |
|---|---|---|
| CN | 201557729 | 8/2010 |
| CZ | 2005-627 A3 | 9/2006 |

(Continued)

*Primary Examiner* — Shay Karls
(74) *Attorney, Agent, or Firm* — Oblon, McClelland, Maier & Neustadt, L.L.P.

(57) ABSTRACT

Embodiments include a toothbrush apparatus including an ergonomic handle portion having an axis. The apparatus also includes semi-automatic rotatable bristles disposed in a removable brush block. The apparatus further includes a brush block disposed at a proximal end of a brush block arm and a rotatable brush block arm disposed in a proximal end of a coupling joint. An axis of the brush block arm is angled between 90° to 120° with respect to the axis of the ergonomic handle portion. The coupling joint is coupled at a distal end to a rotor portion configured for rotation about the axis of the ergonomic handle portion. The coupling joint is configured as a double Cardan joint.

20 Claims, 6 Drawing Sheets

(56) References Cited

FOREIGN PATENT DOCUMENTS

| DE | 196 04 057 | 8/1996 |
| DE | 100 55 930 | 5/2002 |
| KR | 10 1422769 | 8/2014 |
| WO | WO 2010/140784 A2 | 12/2010 |

* cited by examiner

ERGONOMIC SEMI-AUTOMATIC ROTATABLE TOOTHBRUSH APPARATUS

BACKGROUND

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

A number of different teeth brushing techniques have evolved with the passing of time. These include, by way of example, the Bass method, the Charter method, and the Modified Stillman method. The Bass method is useful for all types of dental conditions, especially periodontal problems. With brush bristles pointed at a 45° angle into the gingival sulcus, the user vibrates the brush gently back and forth a plurality of times and then moves the brush forward, thereafter the process is repeated.

The Charter Method is useful for patients with severe loss of interdental papilla height, fixed prosthetic appliances, previous gingival surgery, or subsided ulcerative gingivitis. The method includes a first rolling stroke to remove debris from the teeth. Then, the bristle tips are directed toward the occlusal or incisal surfaces of the user's teeth. Next, the handle of the brush is gently rotated, thus flexing the bristles and bringing them into contact with the interdental tissues and exposed proximal surfaces. The brush handle is then vibrated with a slow, circular motion.

The Modified Stillman Method is useful for patients with hypersensitive gingiva or slightly reduced interdental papilla. This technique uses the rolling stroke method while vibrating the bristles in a lateral motion. The rolling stroke method involves placing the brush above the free gingiva with the bristles pointed toward the apices. Then, by exerting a light pressure, the user draws the brush toward the occlusal surface using a rolling stroke.

Nevertheless, these methods and other common tooth brushing techniques and the associated difficulty involved with vigorous tooth brushing often lead to physical fatigue. This fatigue usually develops in the dorsal group of the shoulder muscles due to their relatively important role in controlling the scrub techniques, and due to the way that the hand grasps the toothbrush. Various devices, such as contoured and shaped handles, have been proposed, but such devices have not met with anything more than partial success. Thus, a flexible, ergonomic toothbrush with semi-automatic, replaceable brushes solving the aforementioned problems is desired. U.S. Pat. No. 8,561,248 B2, which is commonly owned or assigned, discloses a flexible, ergonomic toothbrush with replaceable brushes that is configured to reduce stress and strain on the user, and which features a replaceable brush block that is supported on a flexible brush handle arrangement, the contents of which is herein incorporated in its entirety by reference.

SUMMARY

Embodiments include a toothbrush apparatus having an ergonomic handle portion having an axis. The apparatus also includes a rotor portion configured for rotation about the axis of the ergonomic handle portion. The apparatus further includes a rotatable brush block arm and a coupling joint connected to each of the ergonomic handle portion and the rotatable brush block arm. The apparatus also includes a brush block disposed at a proximal end of the rotatable brush block arm. The rotatable brush block arm is disposed at a proximal end of the coupling joint. The coupling joint can be coupled at a distal end to the rotor portion. An axis of the rotatable brush block arm is angled between 90° to 120° with respect to the axis of the ergonomic handle portion and the brush block is configured to extend orthogonal to the ergonomic handle, with bristles extending laterally when facing a front face of the ergonomic handle.

Embodiments also include an apparatus having means for holding a toothbrush. The apparatus also includes means for inserting a brush block into a brush block arm having an axis. The apparatus further means for removing a brush block arm from the toothbrush. The apparatus can also include means for semi-automatically rotating the brush block arm disposed in a coupling joint. The coupling joint is coupled at a distal end to a rotor portion configured for rotation about the axis of the means for holding. The axis of the brush block arm is angled between 90° to 120° with respect to the means for holding. The brush block is configured to extend orthogonal to the means for holding, with bristles extending laterally when facing a front face of the means for holding.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

The present disclosure relates to toothbrushes, and more particularly to an ergonomic toothbrush with a semi-automatic rotatable brush block configured to reduce stress and strain on a user, and which features a replaceable brush block that is supported on a flexible brush arm arrangement including a 90° to 120° angle, for example, with respect to a toothbrush handle grip. In certain embodiments, the flexible brush arm arrangement may include angles less than 90° or greater than 120°.

The present disclosure overcomes all of the above issues related to the use of conventional toothbrushes. For instance, embodiments of the present disclosure include a semi-automatic rotational movement of a brush block of the disclosed toothbrush, having an angle between the handle grip and the brush block, which may vary from a range of 90° to 120° which provided the advantage of more easily reaching the user's back teeth.

The toothbrush of this disclosure is a two-axis toothbrush with a rotatable head configured to clean the teeth of a user and to reach the distal area of the mouth with little or no trauma and less fatigue on the shoulder muscles of the user which may lead to more brushing time and concentration by the user for increased plaque removal. The toothbrush of this disclosure is configured to be used manually and is therefore cheaper than electric toothbrushes and could be used by everyone, especially children and disabled people. Further, the toothbrush of this disclosure may help eliminate faulty tooth brushing techniques.

Thus, the flexible, ergonomic toothbrush with semi-automatic rotatable brush bristles is directed to reducing user fatigue when brushing and reducing the risk of tooth brushing trauma by providing a toothbrush that can reach distant tooth surfaces easily and that can be used by the handicapped, particularly handicapped children. The flexible, ergonomic toothbrush with semi-automatic rotatable brush bristles has a handle, a brush block having bristles extending therefrom, and a brush head configured to rotate the brush block. The brush head arm extends to and is fixed to a coupling joint. The coupling joint may be configured to slidably engage opposite to the arm of the handle grip, which is connected to a slider that holds a divider, and a rotor is configured to rotate the brush head with assistance from a compression spring. In one of the embodiments, the operative positions can face 180° apart. The handle and the brush head arm are connected by the coupling joint, flexible neck that includes a 90° to 120° bend so that the brush block extends orthogonal to the handle, the bristles also extending laterally when facing the front face of the handle.

Figure 1:
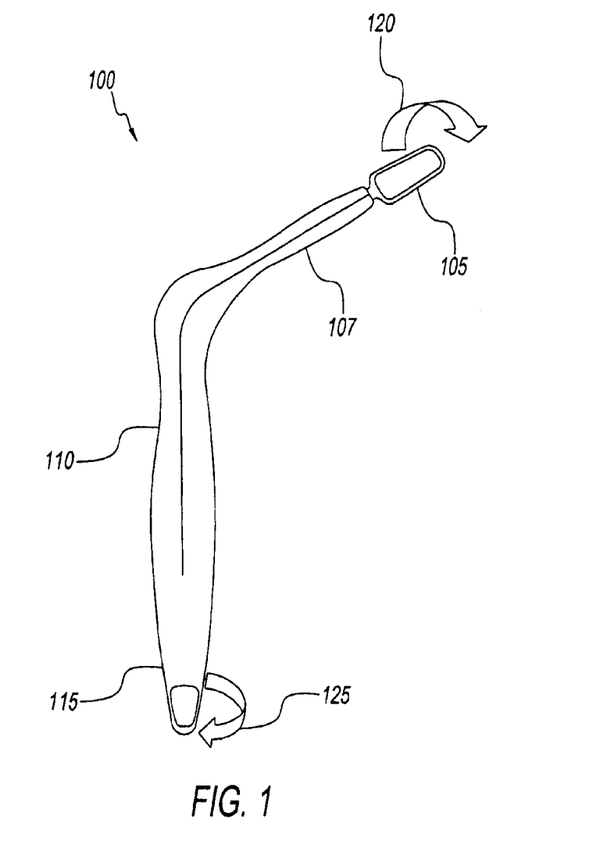
FIG. 1 is an illustrative view of the toothbrush apparatus according to certain embodiments of the disclosure.

FIG. 1 is an illustrative view of the toothbrush apparatus 100 according to certain embodiments of the disclosure. In FIG. 1, toothbrush apparatus 100 includes a brush head portion 105, a flexible arm 107, a handle grip portion 110, and a rotor portion 115. Rotor portion 115 is configured to control the movement of the brush head portion 105. Brush head portion 105 may be configured to be removable. Handle grip portion 110 may be configured as an ergonomic grip to provide a user with a comfortable and sure grip during use.

In certain embodiments, the removable brush head portion 105 is configured to rotate in a direction 120 when rotor portion 115 is engaged by a user to rotate in the same direction 125, as shown by the arrows in FIG. 1. Brush head portion 105 may contain a brush block 106 (see FIG. 4) configured to be replaceable/removable from brush head portion 105. Brush block 106 is configured to hold bundles of bristles. Flexible arm 107 is configured to extend at an angle, for example, between 90° to 120° with respect to handle grip portion 110. Flexible arm 107 is configured to bend so that the brush block 106 extends orthogonal to the handle grip portion 110, the brush block 106 is also configured to extend laterally when facing the front face of the handle grip portion 110.

Figure 2:
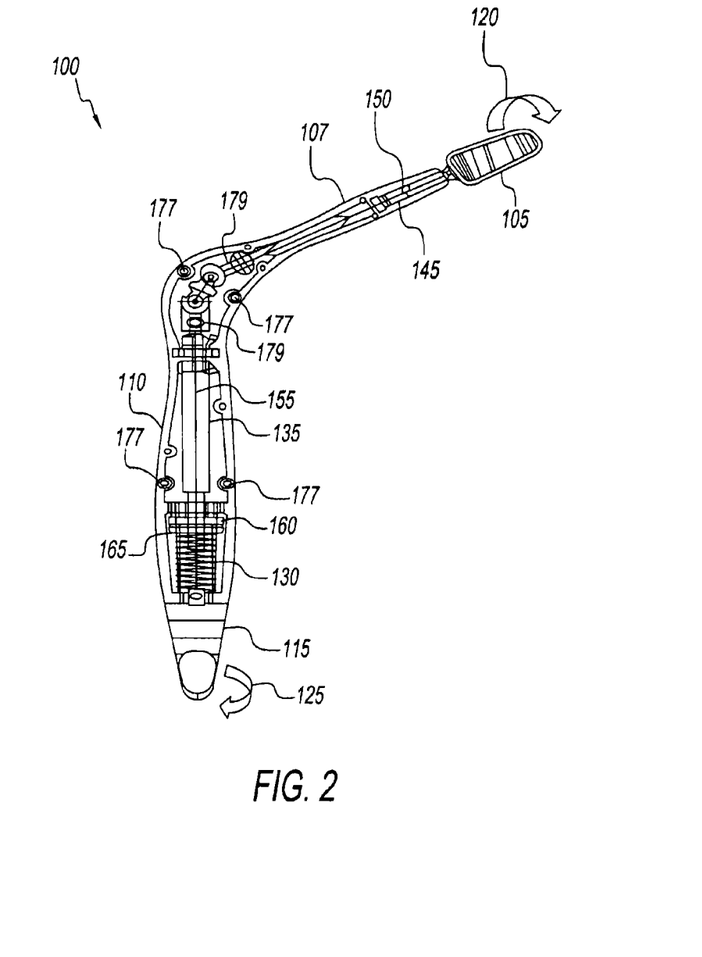
FIG. 2 is a schematic view of the toothbrush apparatus of FIG. 1 according to certain embodiments of the disclosure.

FIG. 2 is a schematic view of the toothbrush apparatus 100 of FIG. 1 according to certain embodiments of the disclosure. In FIG. 2, toothbrush apparatus 100 includes a first rotational axis 150 and a second rotational axis 155. The first rotational axis 150 is disposed proximal brush head portion 105 and the second rotational axis 155 is disposed proximal the handle grip portion 110. Handle grip portion 110 includes a body cavity 170 where internal elements are disposed. Body cavity 170 is a component socket created by the joining of two half covers 110a, 110b (see FIG. 3).

The internal elements of toothbrush apparatus 100 include a compression spring 130, a collar element 165, a divider element 160, a slider element 135, a coupling joint 140, and a brush block arm 145. The divider element 160 may be configured to slidably mount within compression spring 130 and collar element 165. Compression spring 130 is a spring configured to control and set the movement of rotor 115. Divider element 160 is configured to move the slider element 135. The brush head portion 105 and brush block arm 145 are disposed to be coaxial with the first rotational axis 150. The slider element 135, divider element 160, and compression spring 130 are disposed to be coaxial with the second rotational axis 155.

Brush block arm 145 is configured to connect the brush head portion 105 to the coupling joint 140, and to rotate the brush head portion 105 a complete 360° based on the desired position of rotor portion 115 by a user. Handle grip portion 110 may be fastened together via a set of fasteners 177 configured to join half covers 110a, 110b (see FIG. 3). The set of fasteners 177 may be screws to firm-up and secure the half covers 110a, 110b. Slider element 135 is disposed between and inserted into both coupling joint 140 and divider element 160. Slider element 135 is a slider bar configured to connect the divider element 160 for controlling the quarter turn of the brush block arm 145. Coupling joint 140 is a joint configured to connect the brush block arm 145 to the slider 135, and to transfer a 180° rotation between the brush block arm 145 and the slider 135. Coupling joint 140 includes at least two fasteners 179 configured to hold or attach the proximal end 112 of slider element 135 at a first end of coupling joint 140 and a distal end of brush block arm 145 at a second end of coupling joint 140.

Figure 3:
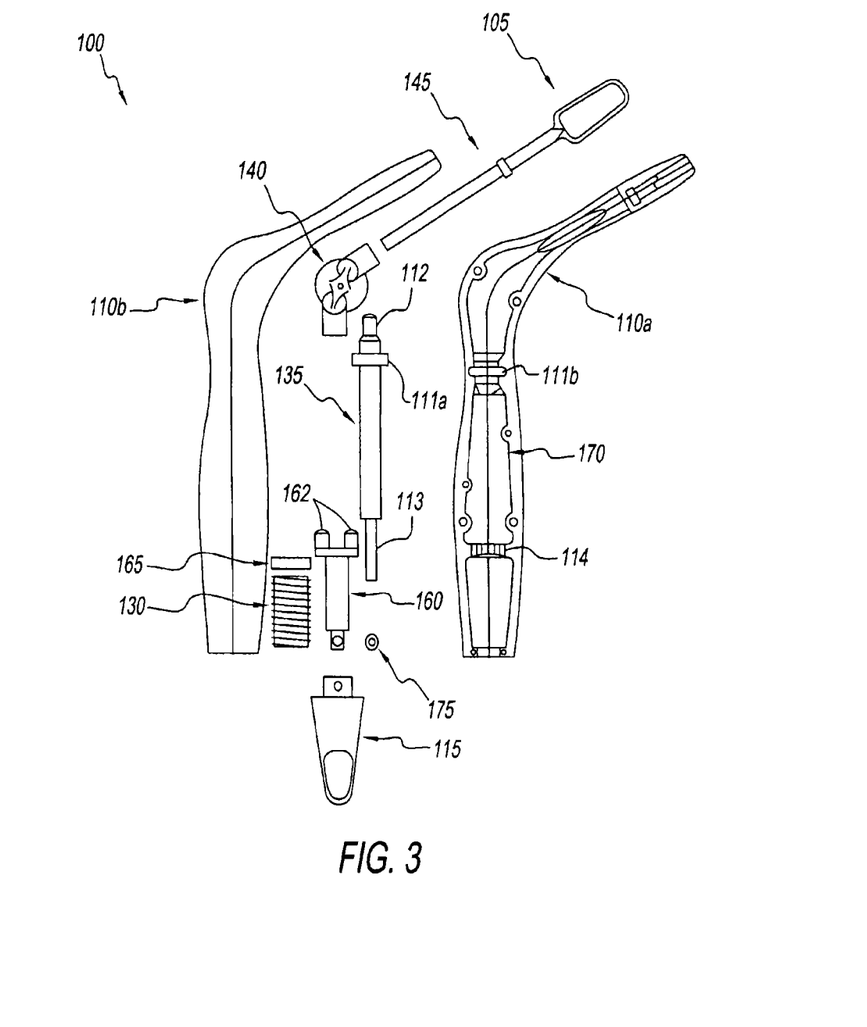
FIG. 3 is an exploded plan view of the toothbrush apparatus of FIG. 1 according to certain embodiments of the disclosure.

FIG. 3 is an exploded plan view of the toothbrush apparatus 100 of FIG. 1 according to certain embodiments of the disclosure. In FIG. 3, toothbrush apparatus 100 includes two fastenable exterior half covers 110a and 110b configured to mesh together upon fastening. Half cover 110a is a first half cover of the toothbrush apparatus 100 which includes a socket for the internal elements. Half cover 110b is a second half cover of the toothbrush apparatus 100 which includes a socket or cavity 170 configured to hold internal elements of toothbrush apparatus 100.

As discussed above, toothbrush apparatus 100 includes internal elements, such as compression spring 130, collar element 165, divider element 160, slider element 135, coupling joint 140, a fastener 175, and brush block arm 145. Collar element 165 is configured to assist controlling the position of brush block portion 105 by frictionally engaging the divider element 160 via contact with compression spring 130. Fastener 175 may include a set screw, self-tapping screw or the like configured to hold components of the divider element 160.

Slider element 135 may include a protruding disc portion 111a configured to engage a disc recess portion 111b disposed in alignment with disc portion 111a within each half cover 110a, 110b. Slider element 135 may also include a proximal end protrusion 112 mountable to a first end of coupling joint 140 and a distal end protrusion 113 mountable within an axial opening in divider element 160.

Half covers 110a, 110b may be configured to include an engagement portion 114 disposed within cavity 170 in alignment with a pair of protrusions 162 disposed on a proximal end of divider element 160. The pair of protrusions 162 is configured to be spaced-apart by about 180°. Protrusions 162 are further configured to snap or lock into position when rotated to an adjoining engagement portion 114 (see FIG. 4).

Divider element 160 and rotor portion 115 are configured to be coupled together for rotational translation from rotor portion 115 via fastener 175. Fastener 175 is configured to attach a distal end of divider element 160 to a proximal end of rotor portion 115. Slider element 135 is configured to have a distal end and a proximal end. Further, slider element 135 is configured to be inserted at its distal end within divider element 160 and inserted within coupling joint 140 at its proximal end. Coupling joint 140 is configured to have at least four degrees of freedom via four pivotal axes. Brush block arm 145 is configured to be inserted into coupling joint 140 opposite divider element 160. Brush block 105a is configured to be set within brush head portion 105.

Figure 4:
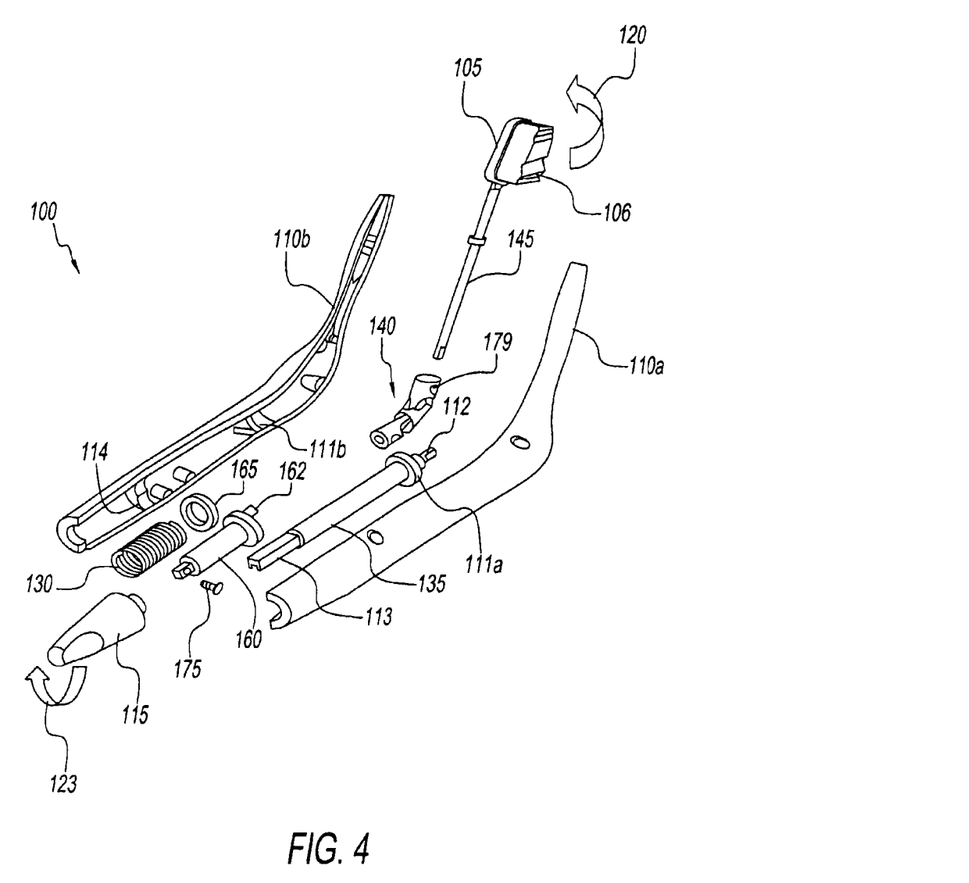
FIG. 4 is an exploded perspective view of the toothbrush apparatus of FIG. 1 according to certain embodiments of the disclosure.

FIG. 4 is an exploded perspective view of the toothbrush apparatus 100 of FIG. 1 according to certain embodiments of the disclosure. In FIG. 4 similar to FIG. 3, toothbrush apparatus 100 has internal elements including compression spring 130 having collar element 165 being disposed about divider element 160. The internal elements also include slider element 135 configured to be mounted at its distal end within divider element 160 for rotational movement and configured to be mounted at its proximal end within coupling joint 140. Coupling joint 140 may be configured to have at least four degrees of freedom about two axes (see FIG. 6B). The internal elements further include brush block arm 145 configured to be mounted at its distal end to coupling joint 140, and fastener 175 configured to attach divider element 160 to rotor portion 115.

Half covers, 110a, 110b are configured to substantially enclose the internal elements discussed above. Brush block arm 145 is configured to hold a brush block 105 disposed at its proximal end. Brush block arm 145 is further configured to rotate in a direction 120 which coincides with a direction of rotation 125 of rotor portion 115.

Figure 5:
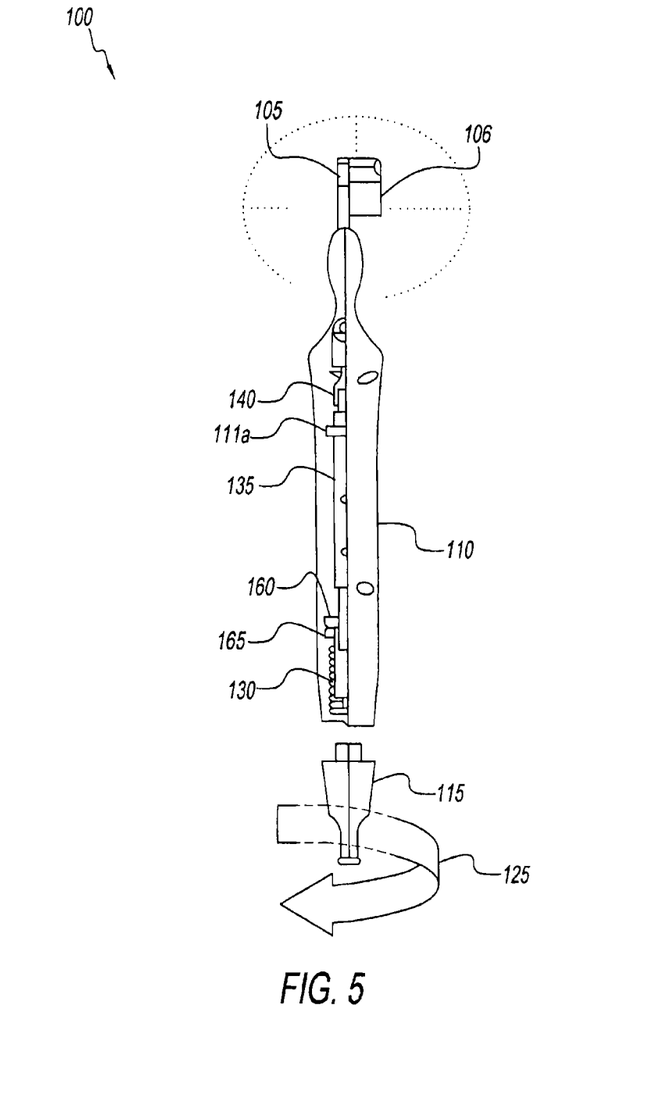
FIG. 5 is a cut-away side view of the toothbrush apparatus of FIG. 1 according to certain embodiments of the disclosure.

FIG. 5 is a cut-away side view of the toothbrush apparatus 100 of FIG. 1 according to certain embodiments of the disclosure. In FIG. 5, toothbrush apparatus 100 shows the relative positions of internal elements which include compression spring 130 having collar element 165, divider element 160 configured to slidably mount within both compression spring 130 and collar element 165, slider element 135, coupling joint 140, brush block 105, and rotor portion 115 configured to rotate in direction 125.

Figure 6A:
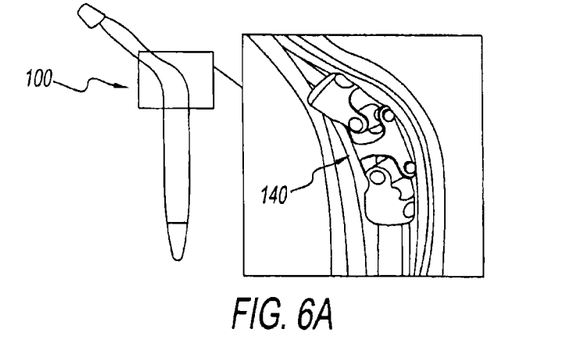
FIGS. 6A to 6C are illustrative views of a coupling joint of the toothbrush apparatus of FIG. 1 according to certain embodiments of the disclosure.
Figure 6B:
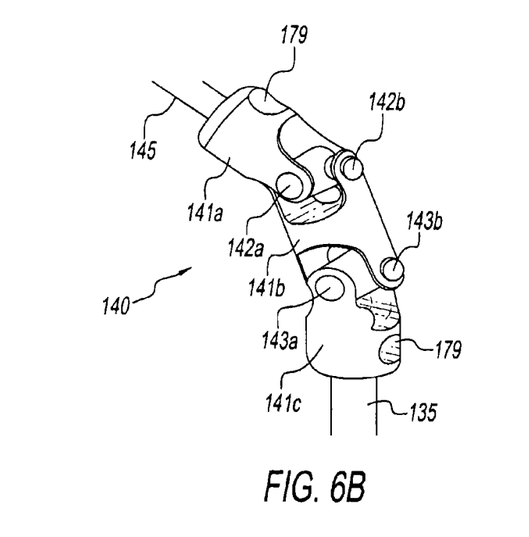
Figure 6C:
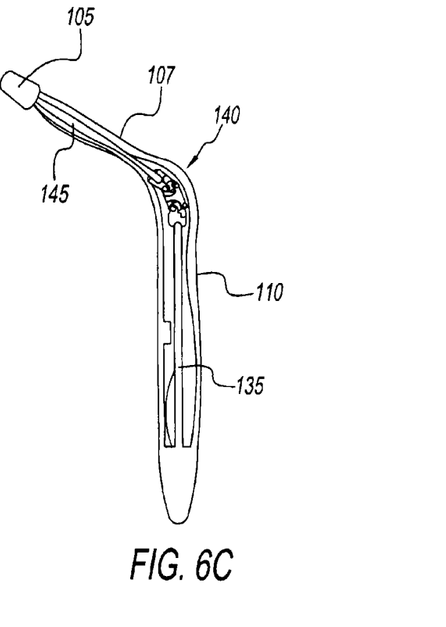

FIGS. 6A to 6C are illustrative views of a coupling joint 140 of the toothbrush apparatus 100 of FIG. 1 according to certain embodiments of the disclosure. In FIG. 6A, toothbrush apparatus 100 is shown with a close-up view of coupling joint 140 displayed in an inset.

In FIG. 6B, coupling joint 140 includes a first portion 141a connected to a middle portion 141b which is connected to a second portion 141c. First portion 141a is connected to at first end of middle portion 141b via two orthogonal intersecting axes 142a and 142b. Second portion 141c is connected to a second end of middle portion 141b via two orthogonal intersecting axes 143a and 143b. Further, first portion 141a is configured to receive brush block arm 145 along axis 150 (see FIG. 2) for rotation. Also, second portion 141c is configured to receive slider element 135 along axis 155 (see FIG. 2) for rotation. This configuration of coupling joint 140 is also known as a double Cardan universal joint where axes 142b and 143b must remain parallel to each other in order to obtain a constant velocity (CV) joint when transferring rotation from slider element 135 to brush block arm 145. Double Cardan joints require a centering element (at 141b) that will maintain equal angles between the driven and driving shafts (at 135 and 145, respectively) for true constant velocity rotation.

In FIG. 6C, a cut-away view of toothbrush apparatus 100 is shown, including the relative positioning of brush block 105, brush block arm 145, coupling joint 140, and slider element 135 with respect to one another within toothbrush apparatus 100.

In some embodiments, toothbrush apparatus 100 may include a flexible arm portion disposed between the coupling joint 140 and the brush block 105 to relieve pressure at the bristle's point of contact with a user. This flexible arm may be configured to as a smooth rubber or soft plastic material or as an accordion-like structure for flexibility.

Alternatively, coupling joint 140 may be replaced with a beveled gear arrangement to provide rotation to brush block arm 145 via rotor portion 115 and slider element 135. However, with a beveled gear arrangement the 90° to 120° angle of the flexible arm 107 may be fixed or set to accommodate the fixed gears.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The above disclosure also encompasses the embodiments noted below.

(1) A toothbrush apparatus, comprising: an ergonomic handle portion having an axis; a rotor portion configured for rotation about the axis of the ergonomic handle portion; a rotatable brush block arm; a coupling joint connected to each of the ergonomic handle portion and the rotatable brush block arm; and a brush block disposed at a proximal end of the rotatable brush block arm, wherein the rotatable brush block arm is disposed at a proximal end of the coupling joint, wherein the coupling joint is coupled at a distal end to the rotor portion, and wherein an axis of the rotatable brush block arm is angled between 90° to 120° with respect to the axis of the ergonomic handle portion and the brush block is configured to extend orthogonal to the ergonomic handle, with bristles extending laterally when facing a front face of the ergonomic handle.

(2) The toothbrush apparatus according to (1), wherein the rotatable brush block arm is configured to be manually controlled via the rotor portion disposed in the ergonomic handle portion.

(3) The toothbrush apparatus according to (1) or (2), wherein the rotor portion is coupled to a spring-loaded divider, a slider, and the coupling joint disposed proximal the 90° to 120° angle.

(4) The toothbrush apparatus according to any one of (1) to (3), wherein the ergonomic handle portion includes a first half cover and a second half cover configured to enclose the spring-loaded divider, the slider, and the coupling joint.

(5) The toothbrush apparatus according to any one of (1) to (4), wherein the coupling joint is configured as a double Cardan joint.

(6) The toothbrush apparatus according to any one of (1) to (5), wherein the coupling joint is configured as a constant velocity (CV) joint.

(7) The toothbrush apparatus according to any one of (1) to (6), wherein the rotatable brush block arm is disposed within a flexible arm portion.

(8) The toothbrush apparatus according to any one of (1) to (7), wherein the double Cardan joint includes four axes, two of the four axes are configured to remain parallel to one another during rotation of the double Cardan joint.

(9) The toothbrush apparatus according to any one of (1) to (8), wherein the rotor portion is configured to be spring loaded.

(10) The toothbrush apparatus according to any one of (1) to (9), wherein the spring is a compression spring disposed about an axis of the rotor portion.

(11) The toothbrush apparatus according to any one of (1) to (10), wherein the axis of the ergonomic handle portion intersects the axis of the brush block arm.

(12) The toothbrush apparatus according to any one of (1) to (11), wherein the brush block is configured to be removable from the brush block arm.

(13) The toothbrush apparatus according to any one of (1) to (12), wherein the axis of the ergonomic handle portion and the axis of the brush block arm intersect proximal the coupling joint.

(14) The toothbrush apparatus according to any one of (1) to (13), wherein the coupling joint is configured to pivot between 90° to 120° during rotation of the rotor portion.

(15) The toothbrush apparatus according to any one of (1) to (14), wherein the rotor portion, the spring-loaded divider, and the slider are coaxial.

(16) The toothbrush apparatus according to any one of (1) to (15), wherein the rotatable brush block arm is configured for semi-automatic rotation via the rotor portion.

(17) An apparatus, comprising: means for holding a toothbrush; means for inserting a brush block into a brush block arm having an axis; means for removing a brush block arm from the toothbrush; and means for semi-automatically rotating the removable brush block arm disposed in a coupling joint, wherein the coupling joint is coupled at a distal end to a rotor portion configured for rotation about the axis of the means for holding, wherein the axis of the brush block arm is angled between 90° to 120° with respect to the means for holding, and wherein the brush block is configured to extend orthogonal to the means for holding, with bristles extending laterally when facing a front face of the means for holding.

(18) The apparatus according to (17), wherein the brush block arm is configured to be manually controlled via the rotor portion disposed in the ergonomic handle portion.

(19) The apparatus according to (17) or (18), wherein the coupling joint is configured as a double Cardan joint.

(20) The apparatus according to any one of (17) to (19), wherein the rotor portion is coupled to a spring-loaded divider, a slider, and a coupling joint disposed proximal the 90° to 120° angle.

The invention claimed is:

1. A toothbrush apparatus, comprising:
an ergonomic handle portion having an axis;
a rotor portion configured for rotation about the axis of the ergonomic handle portion;
a rotatable brush block arm;
a coupling joint connected to each of the ergonomic handle portion and the rotatable brush block arm; and
a brush block disposed at a proximal end of the rotatable brush block arm,
wherein the rotatable brush block arm is disposed at a proximal end of the coupling joint,
wherein the coupling joint is coupled at a distal end to the rotor portion, and
wherein an axis of the rotatable brush block arm is angled between 90° to 120° with respect to the axis of the ergonomic handle portion and the brush block is configured to extend orthogonal to the ergonomic handle, with bristles extending laterally when facing a front face of the ergonomic handle.

2. The toothbrush apparatus according to claim 1, wherein the rotatable brush block arm is configured to be manually controlled via the rotor portion disposed in the ergonomic handle portion.

3. The toothbrush apparatus according to claim 1, wherein the rotor portion is coupled to a spring-loaded divider, a slider, and the coupling joint disposed proximal the 90° to 120° angle.

4. The toothbrush apparatus according to claim 3, wherein the ergonomic handle portion includes a first half cover and a second half cover configured to enclose the spring-loaded divider, the slider, and the coupling joint.

5. The toothbrush apparatus according to claim 3, wherein the rotor portion, the spring-loaded divider, and the slider are coaxial.

6. The toothbrush apparatus according to claim 1, wherein the coupling joint is configured as a double Cardan joint.

7. The toothbrush apparatus according to claim 6, wherein the double Cardan joint includes four axes, two of the four axes are configured to remain parallel to one another during rotation of the double Cardan joint.

8. The toothbrush apparatus according to claim 1, wherein the coupling joint is configured as a constant velocity (CV) joint.

9. The toothbrush apparatus according to claim 1, wherein the rotatable brush block arm is disposed within a flexible arm portion.

10. The toothbrush apparatus according to claim 1, wherein the rotor portion is configured to be spring loaded.

11. The toothbrush apparatus according to claim 9, wherein the spring is a compression spring disposed about an axis of the rotor portion.

12. The toothbrush apparatus according to claim 10, wherein the axis of the ergonomic handle portion intersects the axis of the rotatable brush block arm.

13. The toothbrush apparatus according to claim 1, wherein the brush block is configured to be removable from the rotatable brush block arm.

14. The toothbrush apparatus according to claim 1, wherein the axis of the ergonomic handle portion and the axis of the rotatable brush block arm intersect proximal the coupling joint.

15. The toothbrush apparatus according to claim 1, wherein the coupling joint is configured to pivot between 90° to 120° during rotation of the rotor portion.

16. The toothbrush apparatus according to claim 1, wherein the rotatable brush block arm is configured for semi-automatic rotation via the rotor portion.

17. An apparatus, comprising:
means for holding a toothbrush;
means for inserting a brush block into a brush block arm having an axis;

means for removing a brush block arm from the toothbrush; and means for semi-automatically rotating the brush block arm disposed in a coupling joint, wherein the coupling joint is coupled at a distal end to a rotor portion configured for rotation about the axis of the means for holding, wherein the axis of the brush block arm is angled between 90° to 120° with respect to the means for holding, and wherein the brush block is configured to extend orthogonal to the means for holding, with bristles extending laterally when facing a front face of the means for holding.

18. The apparatus according to claim 17, wherein the brush block arm is configured to be manually controlled via the rotor portion disposed in the means for holding.

19. The apparatus according to claim 17, wherein the coupling joint is configured as a double Cardan joint.

20. The apparatus according to claim 17, wherein the rotor portion is coupled to a spring-loaded divider, a slider, and a coupling joint disposed proximal the 90° to 120° angle.

* * * * *